United States Patent [19]

Versaggi et al.

[11] Patent Number: 4,465,062
[45] Date of Patent: Aug. 14, 1984

[54] NONINVASIVE SEAL FOR A SUCKING CHEST WOUND

[76] Inventors: Gina Versaggi, 405 Roselawn Blvd., Lafayette, La. 70503; Anthony St. Germain, 1022 No. David Dr., Abbeville, La. 70510

[21] Appl. No.: 378,065

[22] Filed: May 14, 1982

[51] Int. Cl.$^3$ ............................................. A61M 1/00
[52] U.S. Cl. .................................. 128/1 R; 604/122; 604/247; 128/207.16
[58] Field of Search .................... 128/1 R, 207.16; 604/8-10, 19, 49, 51, 93, 247, 175, 236, 237, 344, 333, 122

[56] References Cited

U.S. PATENT DOCUMENTS

| | | | |
|---|---|---|---|
| 733,152 | 7/1903 | Chisholm | 604/247 |
| 2,867,213 | 1/1959 | Thomas, Jr. | 604/247 |
| 3,020,913 | 2/1962 | Heyer | 604/247 X |
| 3,463,159 | 8/1969 | Heimlich | 604/247 |
| 3,542,026 | 11/1970 | Bledsoe | 604/247 X |
| 3,777,757 | 12/1973 | Gray et al. | 604/247 X |
| 4,153,058 | 5/1979 | Nehme | 604/247 X |
| 4,170,231 | 10/1979 | Collins | 604/333 X |
| 4,213,458 | 7/1980 | Nolan et al. | 604/344 |

Primary Examiner—C. Fred Rosenbaum
Assistant Examiner—Michelle N. Lester
Attorney, Agent, or Firm—Thomas S. Keaty

[57] ABSTRACT

A noninvasive seal for a sucking chest wound has a rectangular base portion with an aperture in its center, and which is covered with an adhesive substance on its bottom surface. A one-way check valve has an outwardly extending horizontal flange at its lowermost portion, this flange is mounted on the underside of the base portion around the aperture in such a matter that a central opening in the valve body and the aperture in the base portion register with each other. The body of the check valve is made of a Teflon coated rubber to prevent blood from adhering to its inner walls. A seal ring made of Karaya-type gum having a diameter approximately equal to the length of the flange is mounted under the flange, and by adhering to it assures a fixed position of the check valve about the base and therefore about a wound. A dome shaped cap made of a noncollapsible plastic is mounted in covering relationship to the valve directly to the base portion by means of an adhesive applied to its flanges located on the lowermost portion of the dome and extending horizontally in parallel relationship to the base. A plurality of bayonet air slots are made around the periphery of the top portion of the cap to facilitate expellment of air (which has been trapped in a chest cavity) after it exits through a slot in the check valve. The adhesive bottom surface of the base and the seal ring is covered with the protective cover which is peeled off prior to mounting of the device on a patient's body.

1 Claim, 6 Drawing Figures

NONINVASIVE SEAL FOR A SUCKING CHEST WOUND

FIELD OF THE INVENTION

The present invention relates to a noninvasive seal for treating sucking chest wounds which encompasses a base provided with a cap which encloses a one-way check valve which prevents air from being collected and trapped in the chest cavity by allowing the escape of air upon forceful expiration and which prevents the entry of air into the chest cavity generally associated with a sucking chest wound.

BACKGROUND OF THE INVENTION

1. Field of the Invention

The present invention relates to a noninvasive seal for treating sucking chest wounds comprising a base provided with a cap which provides an effective seal for the wound, thereby enabling the victim to breath normally. The cap would enclose a one-way check valve for allowing the escape of air which oftentimes forms in pockets in the chest cavity in conjunction with a sucking chest wound.

2. General Background

The present invention relates generally to an improved, noninvasive seal for a sucking chest wound. Although conventional seals for sucking chest wounds do provide a means for sealing the wound they do not allow for the escape of air that oftentimes collects in the chest cavity beneath the seal. It is a primary objective of the present invention to prevent this problem from occurring. Also, the present invention has as one of its aims a more effective seal, thereby preventing any slippage or movement of the bandage around the wound.

A sucking chest wound is any puncture of the chest which results in impaired breathing due to air entering the chest cavity via this puncture vis-a-vis entering through the mouth and down the trachae, etc. to the lungs, which is the normal air intake method.

Many types of bandages are presently utilized to treat sucking chest wounds, the most common means being vaseline gauze, plastic wrap, aluminum foil, etc. However, none provides a one-way check valve which facilitates the passage of air from the chest cavity to the outside, so as to prevent air from collecting within the chest cavity. Trapped air in the chest cavity is very painful and can cause disorders which seriously hamper the normal respiratory and/or cardiac functions (e.g., collapse of a lung). The conventional method which attempts to deal with this problem is to attach vaseline gauze, plastic wrap, aluminum foil, or like materials over the wound and secure it thereto by means of adhesive tape. However, in a significant number of cases, the problem of trapped air in the chest cavity has *not* been alleviated. The present invention overcomes these shortcomings of the prior art by providing a one-way check valve. The check valve is provided with a slot in the top end which remains closed until sufficient air pressure from the chest cavity forces it open, thereby allowing the escape of air therefrom. A cap is mounted onto the bandage, which encloses the check valve. A ring seal secures the cap to the bandage, thereby ensuring that the bandage does not leak or move around the wound.

The above brief description, as well as further objects, features and advantages of the present invention will be more fully appreciated by reference to the following detailed description of the presently preferred, but nontheless illustrative embodiment in accordance with the present invention, when taken in conjunction with the accompanying drawings.

3. Description of the Prior Art

U.S. Pat. No. 3,422,817 entitled "Tracheotomy Bandage", issued to S. Mishkin, et. al. The Mishkin patent has as one of its primary objectives the elimination of the requirement of an adhesive attachment to the body, but rather attachment to a tube used in a tracheotomy operation. Its application is under different circumstances than the present invention, as its purpose is to absorb body fluids around an operation opening, whereas the present invention has as its primary objective the sealing of a sucking chest wound and prohibiting air flow into the chest cavity, as such air flow, if allowed, greatly inhibits the normal respiratory functions. Also, note that no check valve, cap, or any other device is used similar to that in the present invention.

U.S. Pat. No. 4,221,215, issued to Mandelbaum discloses a surgical dressing used to anchor medical devices, such as chest tubes, to a patient and then to occlude any cut made in a patient for accommodating such medical device. Although the Mandelbaum invention teaches the use of an aperture in the bandage to dispose a device, the device which the invention is designed to embody is a medical device used in surgery, e.g. a tube used in thoracic operations vis-a-vis the one-way check valve of the present invention. Also, the use of the Mandelbaum bandage itself, i.e., to aid thoracic surgery and to occlude the skin opening following such surgery is for different purposes than the present invention.

The majority of the rest of the patents disclose protective covers, U.S. Pat. No. 697,637 discloses a shield for vaccinations, U.S. Pat. No. 2,367,690 discloses a wound protector, U.S. Pat. No. 2,330,693 discloses a shield for pustules from vaccination against smallpox, U.S. Pat. No. 3,234,941 discloses a protective shield, U.S. Pat. No. 2,443,140 discloses a boil cup, U.S. Pat. No. 4,023,569 discloses a device for the protection of wounds. All of these patents teach the use of dome-shaped hollow caps attached to an adhesive bandage which is secured over the vaccination, boil, operation opening, or wound, etc. The dome-shaped caps are employed for protective purposes only. None of these patents are designed to provide an effective seal for sucking chest wounds, and none teach the use of a one-way check valve which would facilitate the expelment of trapped air which collects in the chest cavity.

U.S. Pat. No. 4,212,316, issued to Basch, et. al., teaches a control valve for use in an automotive fuel pump. The valve is controlled by a coil compression spring which seats in a housing. This valve would be impossible to apply in the context of our invention, as the air is emanating from within a human body and a coil compression spring could not operate within the human body.

U.S. Pat. No. 3,336,942, issued to G. & C. Keith, relates to a check valve for use in preventing reverse flow of fluids in vessels or pipes. A poppet and reinforcing coil arranged for axial movement within a pipe, the pressure of the fluid forcing the poppet to apply tension to the coil and expand same. Such an arrangement is unsuitable for the purposes of the present invention, as such an arrangement would be impossible to apply within the configuration of any wound protecter and in conjunction with a human body.

The rest of the patents are merely representative of what in the prior art.

DETAILED DESCRIPTION OF THE PREFERRED EMBODIMENT

Figure 2:
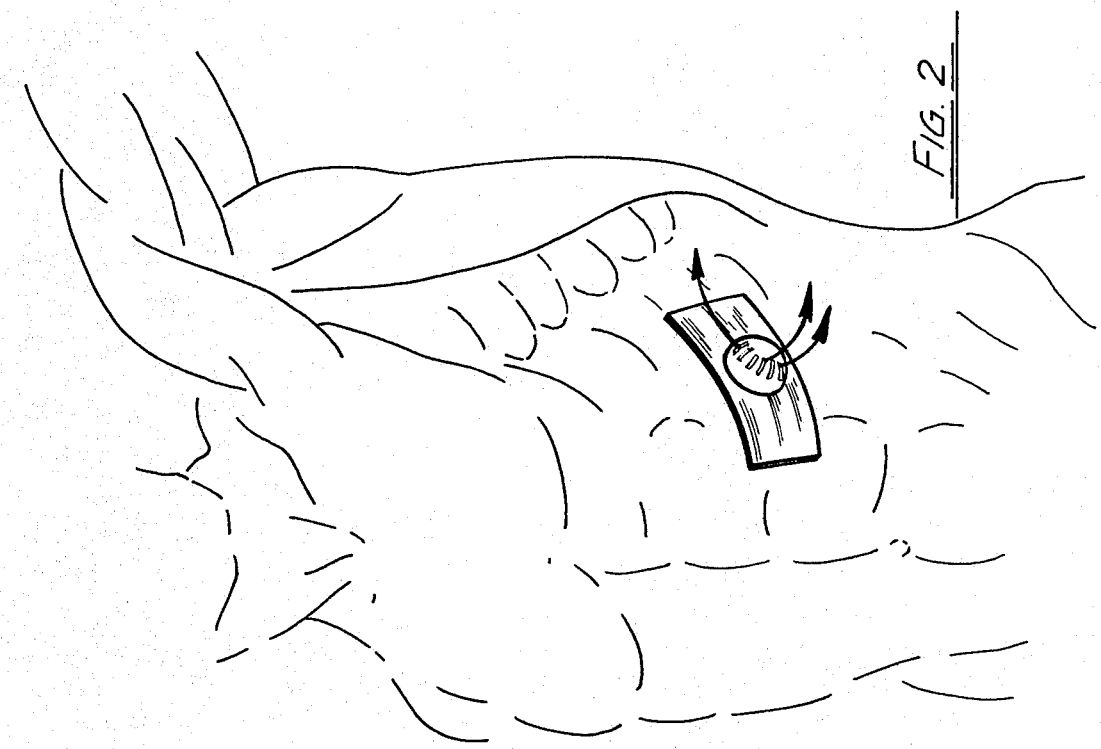
FIG. 2 is an elevated, frontal view of the victim's thoracic upper-body region and depicts the application of the present invention in sealing relation to the sucking chest wound.
Figure 1:
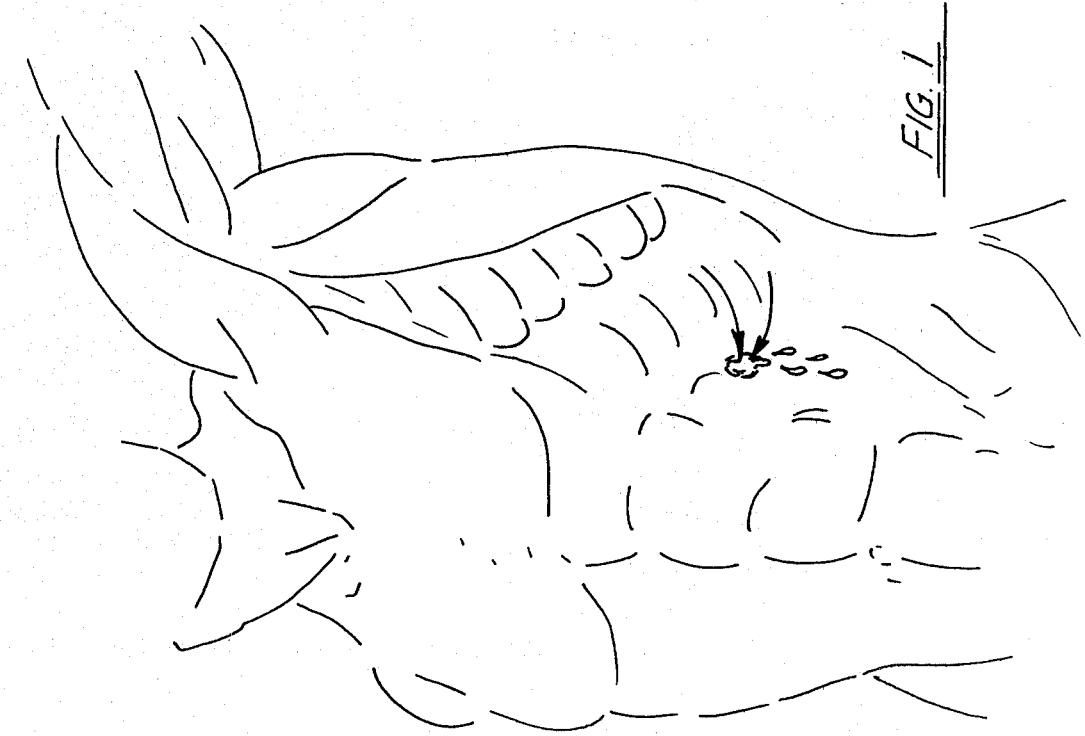
FIG. 1 is an elevated, frontal view of a victim's thoracic upper body region (sucking chest wound), the arrows therein pointing to a puncture in the victim's chest, said puncture being hereinafter referred to as a sucking chest wound.

FIG. 1 illustrates a victim's thoracic region with a sucking chest wound and FIG. 2 illustrates the application of the present invention over the wound.

Figure 6:
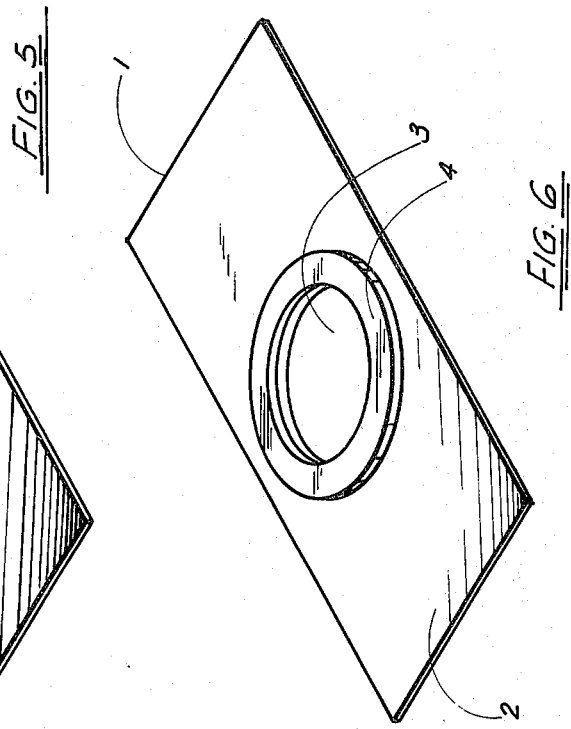
FIG. 6 is a bottom view of the apparatus of the present invention showing the base portion and the ring seal.

Referring to FIG. 6, the base of the present invention is an adhesive bandage 1 with its underside 2 coated with an adhesive for adhering to the victim's skin in surrounding relation to the wound. A series of paper or plastic tabs 14 is provided on the underside 2 of the base which are removable for exposing the adhesive coating of the underside 2. The base 1 defines an aperture 3. An adhesive ring seal 4 provided with an aperture fits securely around the aperture 3 of the base 1 so as to provide a means to ensure that the base 1 does not move about the wound, but rather remains in a fixed position in surrounding relation thereto.

The ring seal 4 is preferably made of karaya-type gum which adheres at the underside of base 1 to flange 16 of check valve 5, horizontally extending outwardly in surrounding relationship to the bottom part of check valve 5 and central aperture 3 of base 1.

It should be noted that the inner diameter of the ring seal 4 is equal to the diameter of central bore 9 of check valve 5 and to the diameter of aperture 3 of base portion 1.

Figure 4:
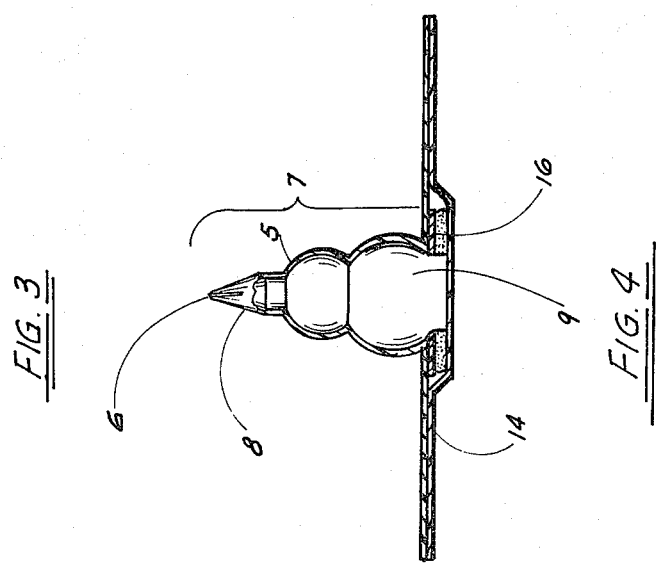
FIG. 4 is a cross-sectional, elevated side view of the check valve disposed in the base.

Referring to FIG. 4, a teflon-coated check valve 5 is disposed securely within the aperture of the seal 4. The Teflon-coated rubber check valve has certain advantages over similar devices presently known in the market. Its nonsticking surface successfully prevents blood clogging of the slot at the uppermost portion of a check valve, thus allowing a long period of continuous operation of the device in case of an unavailability of professional medical help. All other devices suffer from the problem of blood clogging and require constant supervision and substitution after the valve has stopped functioning. The check valve 5 is a one-way valve which permits air which has collected in the chest cavity to escape therefrom by means of the air pressure created by the collected air attempting to expel itself from the chest cavity forcing a slot 6 cut into the top of the check valve 5 to open.

Figure 5:
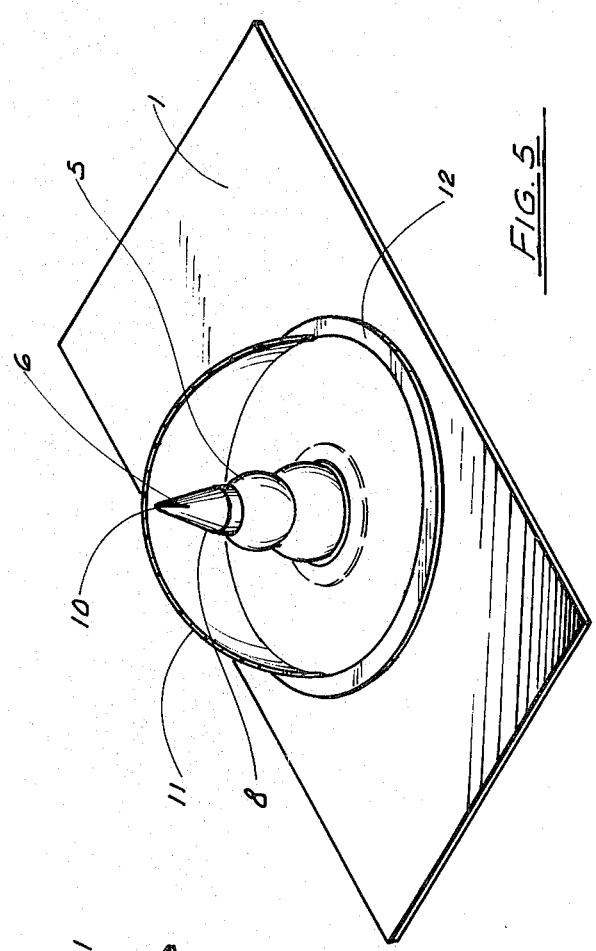
FIG. 5 is a cross-sectional side view of the cap enclosing the check valve disposed in the ring seal, all of which is mounted on the base.
Figure 3:
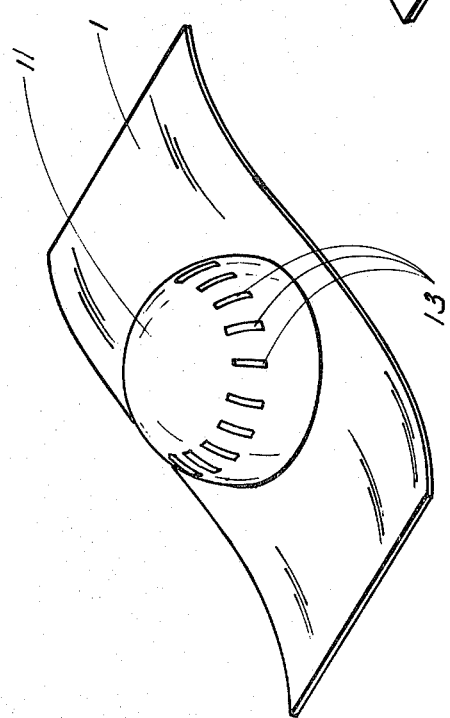
FIG. 3 is a perspective view of the entire invention.

Check valve 5 comprises a circular flange 16 integrally connected to body 7 at its lowermost portion and extending horizontally and outwardly through aperture 3 in the base to the underside of base 1. It should be noted that the flange is sealed by heat to the underside of the base and is adhered to the upper surface of ring seal 4 in such a matter that flange 16 becomes securedly attached between base 1 and ring seal 4. As can be seen in FIG. 4, the length of flange 16 is equal to the width of ring seal 4. The body 7 of the check valve is of generally polygonal shape, terminating in an upper end, conical section 8 with a slot 6 cut into the top thereof, as seen in FIG. 5. A removable, plastic, or any other suitable material, hollow cap 11, as seen in FIG. 3, is placed over the check valve 5 and attached to the adhesive bandage base 1, by means of an adhesive located on the upper surface of the base 1, as seen in FIG. 5, or any other suitable means. In the preferred embodiment, the dome 11 is provided with a flange portion 12 at its lowermost part, the flange extends outwardly in parallel relationship to base 1 and is affixed to the base by means of suitable adhesive or similar means. In such manner, the dome 11 becomes fixably attached in relation to base 1 and check valve 5. The dome 11 is provided with a plurality of bayonet air-slots 13, as seen in FIG. 3, arranged in a horizontal row around the perimetry of the top part of the dome 11, which facilitate the expelment of air from within the chest cavity after it exits the slot 6 of the check valve 5 and thus, to the outside atmosphere. A teflon-coated mushroom tube (not shown) may optionally be inserted into the cylindrical base 16 of the check valve 5, thus forming a new check valve base which would be inserted under the skin of the wound of the victim for damaged tissue expansion.

What is claimed as invention is:

1. A noninvasive seal for a sucking chest wound, which comprises:
   a. A rectangular flexible base means having an aperture in the center and having its bottom surface covered with a layer of an adhesive material adapted to be adhered to a patient's body in surrounding relationship to the wound;
   b. a self-adhering ring seal means securedly attached at the underside of said base means in surrounding relationship to said central aperture and having its inner diameter equal to that of said aperture to further insure a fixed position of said base means in relation to the wound and to further prevent leaking of fluid from the wound and leaking of air into the wound;
   c. a one-way check valve means, made of a Teflon-coated rubber, fixedly disposed on said base means, said valve means having its central bore in the registered relationship with said aperture in said base means, said valve means permitting a continuous expellment of air from a chest cavity of the patient exterially through said aperture in the base means and said central bore in said check valve means and prohibiting the intake of air into the chest cavity, said valve comprising a circular flange means horizontally extending from its lowermost portion through the aperture in said base means to the underside of said base means between the bottom surface of said base means and the upper surface of said seal means, the length of said flange means being substantially equal to the width of said ring seal means, said check valve further comprising a body integrally connected to said flange means, said body having a generally polygonal shape, and which terminates in an upper end conical section which is provided with a slot through the top thereof to permit air which has collected in the chest cavity to escape therefrom;
d. a dome shaped, non-collapsible cap means securedly attached to said base means in covering surrounding relationship to said valve means, said cap means having a plurality of apertures adjacent its top portion to facilitate expoundment of air from said chest cavity after the air has passed through a slot in the uppermost portion of said check valve means, and to serve as a protective shield for said wound.

* * * * *